United States Patent
Beck et al.

(10) Patent No.: US 9,220,261 B1
(45) Date of Patent: Dec. 29, 2015

(54) VOLATILE BLENDS AND THE EFFECTS THEREOF ON THE NAVEL ORANGEWORM MOTH

(75) Inventors: John J. Beck, Rocklin, CA (US); Bradley S. Higbee, Bakersfield, CA (US)

(73) Assignees: The United States of America, as represented by the Secretary of Agriculture, Washington, DC (US); Wonderful Orchards LLC, Los Angeles, CA (US)

( * ) Notice: Subject to any disclaimer, the term of this patent is extended or adjusted under 35 U.S.C. 154(b) by 631 days.

(21) Appl. No.: 13/312,981

(22) Filed: Dec. 6, 2011

Related U.S. Application Data

(60) Provisional application No. 61/420,163, filed on Dec. 6, 2010, provisional application No. 61/560,212, filed on Nov. 15, 2011.

(51) Int. Cl.
| | | |
|---|---|---|
| *A01N 25/00* | (2006.01) | |
| *A01N 27/00* | (2006.01) | |
| *A61K 31/22* | (2006.01) | |
| *A01N 37/14* | (2006.01) | |
| *A61K 31/60* | (2006.01) | |

(52) U.S. Cl.
CPC ............ *A01N 27/00* (2013.01); *A01N 37/14* (2013.01); *A61K 31/60* (2013.01)

(58) Field of Classification Search
CPC ........ A01N 27/00; A01N 37/14; A61K 31/60
See application file for complete search history.

(56) References Cited

PUBLICATIONS

Beck et al., J Sci Food Agric, 2008, 88, 1363-1368.*
Beck et al., J Agric Food Chem, 2012, 60, 8090-8096.*
Dibble, 2008, 1-3.*

* cited by examiner

*Primary Examiner* — Kyle Purdy
(74) *Attorney, Agent, or Firm* — David L. Marks; John D. Fado; Lesley Shaw

(57) ABSTRACT

The present invention relates to formulations of volatile organic compounds having effects on the navel orangeworm moth (NOW). In some embodiments, the blends of volatile organic compounds attract navel orangeworm moths. In other embodiments, the blends disrupt ovipositional activity of the female NOW. The invention also relates to traps baited with any one or more of the disclosed volatile blends, which are effective for controlling NOW.

4 Claims, No Drawings

VOLATILE BLENDS AND THE EFFECTS THEREOF ON THE NAVEL ORANGEWORM MOTH

RELATED APPLICATIONS

This application claims priority to U.S. Provisional Patent Application Ser. No. 61/420,163, filed Dec. 6, 2010 and U.S. Provisional Patent Application Ser. No. 61/560,212, filed Nov. 15, 2011, each of which is incorporated herein by reference in its entirety.

FIELD OF THE INVENTION

The invention relates to attraction and control of insects, particularly the navel orangeworm, *Amyelois transitella*, using blends of volatile organic compounds.

BACKGROUND OF THE INVENTION

The navel orangeworm (NOW), *Amyelois transitella* (Walker) (Lepidoptera: Pyralidae), is a major insect pest in California affecting fruit e.g., figs, pomegranate, and also tree nuts e.g., almonds, pistachio. Feeding damage by NOW larvae lowers nut kernel quality resulting in extensive economic loss to the almond industry. Moreover, feeding damage directly contributes to contamination by ubiquitous fungi of tree nut orchards such as e.g., *Aspergillus flavus, Aspergillus parasiticus*, which are capable of producing aflatoxins—a serious food safety problem due to their carcinogenic and teratogenic attributes (see e.g., Campbell et al., 2003; Robens and Cardwell, 2003). Thus, nuts infested with navel orangeworm are unmarketable and cost the tree nut industry dearly.

Therefore, what is needed in the art are effective means for monitoring and controlling navel orangeworm moth and in turn reducing the damage caused by navel orangeworm infestation.

Fortunately, as will be clear from the following disclosure, the present invention provides for these and other needs.

SUMMARY OF THE INVENTION

In one embodiment, the present invention provides blends of volatile organic compounds effective for attracting, trapping and inducing ovipositional disruption in navel orangeworm moth.

Thus in an exemplary embodiment, the invention provides a blend of volatile organic compounds effective for attracting navel orangeworm moth, the blend comprising racemic 1-octen-3-ol (OCOL), ethyl benzoate (ETBN), methyl salicylate (MSAL), and ethyl palmitate (ETPM) wherein, the blend comprises a minimum relative molar ratio of 3:1 for OCOL:ETBN. In one exemplary embodiment, the blend of volatile organic compounds comprises OCOL:ETBN:MSAL:ETPM in relative ratios of 3:1:1:0 respectively. In another exemplary embodiment, the blend of volatile organic compounds comprises OCOL:ETBN:MSAL:ETPM in relative molar ratios of 12:4:4:1 respectively. In another exemplary embodiment, the blend of volatile organic compounds comprises OCOL:ETBN:MSAL:ETPM in relative ratios of 15:5:1:1 respectively. In one exemplary embodiment, the blend of volatile organic further comprises racemic trans-7-methyl-1,6-dioxaspiro[4.5]decane (conophthorin, CONO).

In one exemplary embodiment, the blend of volatile organic compounds comprises 1-octen-3-ol (OCOL), ethyl benzoate (ETBN), methyl salicylate (MSAL), wherein, the blend comprises a minimum relative molar ratio of 3:1 for OCOL:ETBN and further comprises acetophenone (ACEP). Thus, In one exemplary embodiment, the blend of volatile organic compounds comprises OCOL:ETBN:MSAL:ETPM:ACEP in relative ratios of 12:4:4:0:1, respectively.

In one exemplary embodiment, the blend of volatile organic compounds comprises 1-octen-3-ol (OCOL), ethyl benzoate (ETBN), and methyl salicylate (MSAL) wherein, the blend comprises a minimum relative molar ratio of 3:1 for OCOL:ETBN, acetophenone (ACEP) and conophthorin (CONO). Thus, in one exemplary embodiment, the blend of volatile organic compounds comprises 1-octen-3-ol (OCOL):ethyl benzoate (ETBN):methyl salicylate (MSAL):acetophenone (ACEP):conophthorin (CONO) in a 12:4:4:1:1 molar ratio.

In one exemplary embodiment, the blend of volatile organic compounds comprises 1-octen-3-ol (OCOL), ethyl benzoate (ETBN), and methyl salicylate (MSAL) wherein, the blend comprises a minimum relative molar ratio of 3:1 for OCOL:ETBN, acetophenone (ACEP), 2-phenylethanol, nonanal (NOAL) and humulene. Thus, in one exemplary embodiment, the blend of volatile organic compounds comprises 1-octen-3-ol (OCOL):ethyl benzoate (ETBN):methyl salicylate (MSAL):acetophenone (ACEP):conophthorin (CONO):2-phenylethanol (2PEA):nonanal (NOAL):humulene (HUMU) are present in a 6:1:1:2:2:1:1:2 molar ratio.

In one exemplary embodiment, the blend of volatile organic compounds comprises1-octen-3-ol (OCOL), ethyl benzoate (ETBN), and methyl salicylate (MSAL) wherein, the blend comprises a minimum relative molar ratio of 3:1 for OCOL:ETBN, acetophenone (ACEP) and conophthorin (CONO) and ethyl palmitate. Thus, in one exemplary embodiment, the blend of volatile organic compounds comprises 1-octen-3-ol (OCOL):ethyl benzoate (ETBN):methyl salicylate (MSAL):acetophenone (ACEP):conophthorin (CONO):ethyl palmitate are present in a 12:4:4:1:2:1 molar ratio.

In one exemplary embodiment, the blend of volatile organic compounds comprises 1-octen-3-ol (OCOL), ethyl benzoate (ETBN), and methyl salicylate (MSAL) wherein, the blend comprises a minimum relative molar ratio of 3:1 for OCOL:ETBN, acetophenone (ACEP):conophthorin (CONO) and limonene (LIMO). Thus, in one exemplary embodiment, the blend of volatile organic compounds comprises 1-octen-3-ol (OCOL):ethyl benzoate (ETBN):methyl salicylate (MSAL):acetophenone (ACEP):conophthorin (CONO):limonene (LIMO) are present in a 12:4:0:1:1:3 molar ratio.

In one exemplary embodiment, the invention provides trap for attracting male navel orangeworm, wherein the trap is baited with the blend of volatile organic comprising 1-octen-3-ol (OCOL), ethyl benzoate (ETBN), and methyl salicylate (MSAL) wherein, the blend comprises a minimum relative molar ratio of 3:1 for OCOL:ETBN, acetophenone (ACEP):conophthorin (CONO) and limonene (LIMO).

In one exemplary embodiment, the invention provides a blend of volatile organic compounds effective for attracting navel orangeworm, the blend comprising: limonene:conophthorin:(Z)-ocimene and α-pinene. In one exemplary embodiment the blend of volatile organic compounds comprises: limonene:conophthorin:(Z)-ocimene and α-pinene in a 3:1:1:1 molar ratio.

In one exemplary embodiment, the invention provides a trap for attracting navel orangeworm, wherein the trap is baited with a blend of volatile organic compounds comprising 1-octen-3-ol (OCOL), ethyl benzoate (ETBN), methyl salicylate (MSAL), and ethyl palmitate (ETPM) wherein, the blend comprises a minimum relative molar ratio of 3:1 for OCOL:ETBN.

In one exemplary embodiment, the invention provides a blend of volatile organic compounds effective for attracting navel orangeworm moth, the blend comprising a mixture of, hexanal (HXAL), octanal (OCAL), nonanal (NOAL), 3-octen-2-one (3O2O), in a relative ratio of [4.5-7.5]:[0.5-3.5]:[1.5-4.5]:1. In one exemplary embodiment, the blend of volatile organic compounds of claim 9, wherein the formulation further comprises 7-methyl-1,6-dioxaspiro[4.5]decane (conophthorin, CONO).

In one exemplary embodiment, the invention provides a trap for attracting navel orangeworm, wherein the trap is baited with a blend of volatile organic compounds comprising a mixture of HXAL, OCAL, NOAL, and 3O2O in a relative ratio of [4.5-7.5]:[0.5-3.5]:[1.5-4.5]:1.

Other features, objects and advantages of the invention will be apparent from the detailed description which follows.

DETAILED DESCRIPTION OF THE INVENTION

Definitions

Unless defined otherwise, all technical and scientific terms used herein generally have the same meaning as commonly understood by one of ordinary skill in the art to which this invention belongs.

The term "navel orangeworm" or "navel orangeworm moth" or "NOW" as used herein refer to the organism *Amyelois transitella* (Walker) (Lepidoptera: Pyralidae), a major insect pest of agriculture.

The term "ovipositional disruption" a used herein, refers to distracting or otherwise discouraging a female insect from laying eggs in the usual host plant location (e.g., almond fruit) and to instead lay her eggs in a non-viable location (e.g., an egg trap) in which the resulting larvae do not survive. Thus, in an exemplary embodiment, a volatile blend as disclosed herein is effective for inducing ovipositional disruption in female navel orangeworm. In an exemplary embodiment, ovipositional disruption is observed by comparing the number of NOW eggs laid in an egg trap baited with a volatile blend as disclosed herein comparing that number to the number of egg laid in an unbaited egg trap and observing that the number of eggs laid in the baited trap is greater than the number of eggs laid in the unbaited trap.

The expression "mating disruption" as used herein, refers to interrupting the normal course of an insect reproductive cycle e.g., by luring and/or trapping one or the other or both sexes so that they are removed from the breeding population, such that the insect or insect population generally experiences a reduced probability of successful mating(s). In an exemplary embodiment, mating disruption interferes with the ability of male moths to find and mate with females. In an exemplary embodiment, a volatile blend as disclosed herein is effective for inducing "mating disruption" by attracting female navel orangeworm to traps, thereby removing the females from the breeding population of navel orangeworm. In another exemplary embodiment, a volatile blend as disclosed herein is effective for inducing "mating disruption" by inducing "ovipositional disruption" in mated in female navel orangeworm.

As used herein, the term "control" or "controlling" as in e.g., the phrase: the "control" of navel orangeworm, or "controlling" navel orangeworm, or as in the phrase: "controlling" agricultural pests, refers to any means for preventing infection or infestation, reducing the population of already infected areas or organisms, or elimination of the population of pests or mites or other species whose "control" is desired. Indeed, "controlling" as used herein refers to any indicia of success in prevention, elimination, reduction or amelioration of a pest population or pest problem. In an exemplary embodiment, navel orangeworm is "controlled" by disruption of mating behavior. In another exemplary embodiment disruption of mating behavior affects oviposition of female navel orangeworm.

The term "reduce" as used herein refers to any indicia of success in the diminishment in size, amount, extent, and/or severity of navel orangeworm infestation. The term "reduce" as used herein also refers to any indicia of success in the diminishment of reproductive capacity (e.g., through ovipositional disruption, killing or trapping of females etc); diminishment of spread (e.g., rate or extent of spread) e.g., from an un-treated orchard to a treated orchard; diminished damage to tree nuts caused by navel orangeworm (adults and/or larvae); diminishment of aflatoxin contamination as a result of navel orangeworm presence etc.

As used herein, the term "attracting" refers to the action of causing an insect pest, either directly or indirectly, to move in a direction towards the source of stimulus. One of skill in the art will recognize that suitable stimuli may include a large variety of methods including, but not limited to chemical stimulus e.g., blends of volatile chemicals such as e.g., those disclosed herein, pheromones, kairomones, etc. A chemical stimulus can be an individual compound or a composition, including e.g., more than one compound, that either directly or indirectly, causes the insect to move toward the source of the stimulus. Other attractive stimuli include, but are not limited to thermostimuli, mechanostimuli, visual stimuli e.g., patterns, objects, color, light, and etc.

The term "pheromone" as used herein, refers to a substance or mixture of substances which are secreted and released by an organism for detection and response by another organism of the same species. Pheromones mediate a variety of interactions between organisms. Thus, pheromones are typically classified by the interaction that they most strongly influence e.g., alarm, aggregation or sex pheromone.

As is known in the art, "pheromones" belong to the larger class of chemical compounds referred to as semiochemicals. The term "semiochemical" as used herein refers to chemicals that mediate interactions between organisms. Semiochemicals include allelochemicals and pheromones depending on whether the interactions are interspecific or intraspecific, respectively. As used herein the term "allelochemical" refers to chemical substances that induce a response in the receiver of the signal that is either adaptively favorable to the emitter but not the receiver (allomones), or that is favorable to the receiver but not the emitter (kairomones) or is favorable to both emitter and receiver (synomones). Thus, semiochemicals are useful e.g, as arrestants, attractants, repellents, deterrents, and/or stimulants.

The term "ratio" as used herein, refers to the relative proportion of at least two compounds with respect to one another. Typically, as used herein, the term "ratio" refers to the relative number of moles (molar ratios) present of each compound (not the mass or volume ratios).

The term "tree nuts" is used herein in its broadest sense to include any hard walled, edible kernel produced by trees. Exemplary "tree nuts" include, but are not limited to e.g., pistachio nuts, almonds, Brazil nuts, pine nuts, chestnuts, walnuts, pecans, etc.

The terms "isolated," "purified" or "biologically pure" as used herein, refer to a chemical or microorganism that is substantially or essentially free from components that normally accompany it as found in its native state.

In some exemplary embodiments, the term "isolated" is used to describe an isolated chemical compound, e.g., isolated volatile organic compound. Thus, in some exemplary embodiments, the terms "isolated" or "purified" refer to a chemical species that that is the predominant species present in a preparation. Thus, in some exemplary embodiments, "purity" of an isolated species is determined using analytical chemistry techniques such as e.g., high performance liquid chromatography. A chemical species that is the predominant species present in a preparation is substantially purified. Typically, a "purified" chemical species denotes that a chemical species that is at least about 85% pure, at least about 95% pure, or at least about 99% pure.

As used herein, the term "trap" refers to any device into which the volatile organic blends disclosed herein are placed, and that prevents the insect pest from escaping once the insect pest has come into contact with the trap. The present invention provides traps that can be of various sizes, shapes, colors, and materials. In an exemplary embodiment, traps are designed and manufactured specifically for use as an insect trap (see e.g., U.S. Pat. No. 8,051,600; U.S. Pat. No. 8,028,467, etc). In other exemplary embodiments a trap is a container converted and adapted from other uses such as, for example, a glass Petri dish, a metal coffee can, a cardboard box, or any ordinary plastic, metal, fiberglass, composite or ceramic container. Exemplary materials for use in making the traps include, but are not limited to, cardboard, metal, metal alloys, glass, paper, plastic, acrylic, fiberglass, composite, and ceramic. Typically, traps have a bottom, sidewalls, and a top. The bottom, sidewalls and top of the trap can be solid, or be perforated. An exemplary perforated sidewall is a screen. In an exemplary embodiment, traps are configured such that insect pests can enter the trap but are unable to escape once inside the trap. In other exemplary embodiments, traps are commercially available (e.g., from Suterra Inc.)

I. Introduction:

The navel orangeworm (NOW), *Amyelois transitella* (Walker), is an insect pest of inter alia California tree nuts. The NOW infects tree nuts such as e.g., almonds, pistachios walnuts etc, and feeds on the kernel during development. Feeding damage by growing larvae lowers nut kernel quality which, in turn, results in extensive monetary loss to growers, producers, and shippers. Moreover, NOW feeding damage directly contributes to aflatoxin contamination. Aflatoxin is a mycotoxin produced by *Aspergillus flavus* and *A. parasiticus*, ubiquitous fungi in tree nut orchards. Aflatoxin represents a food safety problem due to its carcinogenic and teratogenic attributes.

Until now, there has been no truly efficacious means for controlling or monitoring of NOW. Especially lacking are long term, high quality solutions that are environmentally friendly. Indeed, the only current standard monitoring tool for female NOW is almond meal, an attractant that does not provide consistent efficacy throughout the growing season. The pyrethroid class of insecticides are effective, but have environmental and regulatory problems. Thus, the lack of an efficacious means for control and/or monitoring of NOW is a critical gap in the tools available to both growers and researchers.

Fortunately, as will be disclosed in detail below, it has now been discovered that certain blends of volatile organic compounds (volatile blends) are effective for attraction and/or mating disruption and hence can be used to control navel orangeworm moth. Thus, as disclosed herein, the effective volatile blends can be deployed in the field e.g., almond orchards, pistachio orchards, etc, for the control and/or monitoring of the navel orangeworm moth.

II. Compounds

A. General Methods

Methods disclosed herein utilize routine techniques in the field of chemistry and chemical analysis. Basic texts disclosing the general methods of use in this invention include, e.g., *GC-MSA Practical User's Guide* by Marvin McMaster, Wiley-VCH (1998); *Modern Analytical Chemistry*, by David T. Harvey, McGraw-Hill Science/Engineering/Math (1999).

B. Blends of Volatile Organic Compounds

FAB4.x

In exemplary embodiments, blend formulations, referred to herein as the "FAB4.x series blends", are effective for attracting NOW and/or inducing ovipositional disruption in female NOW and comprise a mixture of 1-octen-3-ol (OCOL), ethyl benzoate (ETBN), methyl salicylate (MSAL), and ethyl palmitate (ETPM). In general, "FAB4.x series blends" comprise 1-octen-3-ol (OCOL), ethyl benzoate (ETBN). In some exemplary embodiments, 1-octen-3-ol (OCOL) and ethyl benzoate (ETBN) are present in a relative ratio of 5:1. In other exemplary embodiments, 1-octen-3-ol (OCOL), ethyl benzoate (ETBN) are present in a relative ratio of 4:1. In other exemplary embodiments 1-octen-3-ol (OCOL), and ethyl benzoate (ETBN) are present in a relative ratio of 3:1. In other exemplary embodiments 1-octen-3-ol (OCOL), and ethyl benzoate (ETBN) are present in a relative ratio of 2:1. In still other exemplary embodiments, 1-octen-3-ol (OCOL) and ethyl benzoate (ETBN) are present in a relative ratio of 1:1.

In some exemplary embodiments, FAB4.x series blends comprise a minimum relative ratio of 3:1 for OCOL:ETBN, wherein the ratio refers to the relative number of moles (molar ratios) present of each compound (not the mass or volume ratios).

The other two components of the FAB4.x series blends, MSAL and ETPM, are present in variable ratios. Thus, in an exemplary embodiment, the formulation FAB4.25 comprises OCOL:ETBN:MSAL:ETPM in relative ratios of 3:1:1:0 respectively. In some exemplary embodiments a FAB4.x formulation having OCOL:ETBN:MSAL:ETPM in relative ratios of 3:1:1:0 respectively, further comprises acetophenone (ACEP) and conophthorin (chemical name 7-methyl-1,6-dioxaspiro[4.5]decane, CONO). In other exemplary embodiments, a FAB4.x formulation having OCOL:ETBN:MSAL:ETPM in relative ratios of 3:1:1:0 respectively, further comprises acetophenone (ACEP):conophthorin (CONO):2-phenylethanol (2PEA):nonanal (NOAL) and humulene (HUMU). In other exemplary embodiments, a FAB4.x formulation having OCOL:ETBN:MSAL:ETPM in relative ratios of 3:1:1:0 respectively, further comprises acetophenone (ACEP) and conophthorin (CONO) and ethyl palmitate. In other exemplary embodiments, a FAB4.x formulation having OCOL:ETBN:MSAL:ETPM in relative ratios of 3:1:1:0 respectively, further comprises acetophenone (ACEP):conophthorin (CONO) and limonene (LIMO).

In another exemplary embodiment, the formulation FAB4.33 comprises OCOL:ETBN:MSAL:ETPM in relative ratios of 12:4:4:1 respectively. In still another exemplary embodiment, the formulation FAB4.36 comprises OCOL:ETBN:MSAL:ETPM in relative ratios of 15:5:1:1 respectively.

In some exemplary embodiments, FAB4.x series blends further comprise acetophenone (ACEP). Thus, in an exemplary embodiment, a FAB4.x formulation comprises OCOL:ETBN:MSAL:ETPM:ACEP in relative ratios of 12:4:4:0:1, respectively.

Some exemplary compositions of the FAB4.x series blends are shown in Table 1 (below). Other exemplary compositions related to the FAB4.x series blends are disclosed in Examples 3 and 4 hereinbelow.

TABLE 1

Exemplary formulations and ratios for the FAB4.x series.

| | Volatile Component | | | | |
|---|---|---|---|---|---|
| BLND | OCOL | ETBN | MSAL | ETPM | ACEP |
| FAB4.2 | 4 | 2 | 2 | 1 | |
| FAB4.7 | 5 | 2 | 2 | 1 | |
| FAB4.8 | 5 | 3 | 2 | 1 | |
| FAB4.9 | 6 | 2 | 2 | 1 | |
| FAB4.10 | 6 | 3 | 2 | 1 | |
| FAB4.11 | 5 | 3 | 1 | 1 | |
| FAB4.12 | 6 | 3 | 1 | 1 | |
| FAB4.13 | 7 | 3 | 2 | 1 | |
| FAB4.14 | 7 | 2 | 2 | 1 | |
| FAB4.15 | 7 | 2 | 1 | 1 | |
| FAB4.16 | 7 | 3 | 1 | 1 | |
| FAB4.17 | 8 | 2 | 2 | 1 | |
| FAB4.18 | 8 | 2 | 1 | 1 | |
| FAB4.19 | 8 | 3 | 1 | 1 | |
| FAB4.20 | 5 | 3 | 1 | 2 | |
| FAB4.21 | 6 | 3 | 1 | 2 | |
| FAB4.22 | 7 | 3 | 1 | 2 | |
| FAB4.23 | 8 | 3 | 1 | 2 | |
| FAB4.24 | 3 | 1 | 1 | 0 | |
| FAB4.25 | 3 | 1 | 1 | 1 | |
| FAB4.26 | 6 | 2 | 1 | 0 | |
| FAB4.27 | 9 | 3 | 1 | 0 | |
| FAB4.28 | 9 | 3 | 2 | 0 | |
| FAB4.29 | 9 | 3 | 1 | 1 | |
| FAB4.30 | 9 | 3 | 2 | 1 | |
| FAB4.31 | 9 | 3 | 3 | 1 | |
| FAB4.32 | 12 | 4 | 3 | 1 | |
| FAB4.33 | 12 | 4 | 4 | 1 | |
| FAB4.34 | 6 | 4 | 1 | 0 | |
| FAB4.35 | 6 | 4 | 1 | 1 | |
| FAB4.36 | 15 | 5 | 1 | 1 | |
| FAB4.37 | 9 | 5 | 1 | 0 | |
| FAB4.38 | 9 | 5 | 1 | 1 | |
| FAB4.39 | 8 | 3 | 1 | 1 | 1 |
| FAB4.40 | 8 | 3 | 1 | 0 | 1 |
| FAB4.41 | 12 | 4 | 4 | 1 | 1 |
| FAB4.42 | 12 | 4 | 4 | 0 | 1 |
| FAB4.43 | 12 | 4 | 4 | 0 | 2 |
| FAB4.44 | 12 | 4 | 4 | 1 | 2 |
| FAB4.45 | 12 | 4 | 4 | 0 | 3 |
| FAB4.46 | 12 | 4 | 4 | 1 | 3 |
| FAB4.47 | 18 | 6 | 3 | 1 | |
| FAB4.48 | 18 | 6 | 6 | 1 | |
| FAB4.49 | 15 | 10 | 5 | 1 | |
| FAB4.50 | 5 | 5 | 5 | 1 | |
| FAB4.51 | 15 | 5 | 10 | 1 | |

In some exemplary embodiments, FAB4.x series blends are prepared with solvents. In other exemplary embodiments, FAB4.x series blends are prepared neat (volatiles mixed together without the use of a solvent or co-volatile in large proportion).

Although any suitable solvent can be used, volatile analyses of almond orchards revealed that different chemical stages of ethanol were present in several experiments—ethanol (EtOH), acetic acid (AcOH—typically from the oxidation of EtOH by an organism), and ethyl acetate (EtOAc—the chemical reaction and subsequent bonding of acetic acid and ethanol). Therefore, without being bound by theory, it is believed that ethanol and ethyl acetate provide natural solvents for solvating volatile organic series blends. Therefore, in some exemplary embodiments, ethyl acetate (EtOAc) is used as a solvent. In other exemplary embodiments ethanol (EtOH) is used as a solvent.

In some exemplary embodiments, increasing the relative proportion of acetophenone (ACEP) increases the effectiveness of the FAB4.x series blend.

In some exemplary embodiments, FAB4.x series volatile blends are used to attract navel orangeworm moths. In other exemplary embodiments, FAB4.x series blends are used to induce mating disruption in navel orangeworm. In other exemplary embodiments, FAB4.x series blends are used to induce ovipositional disruption in female navel orangeworm moths. In still other exemplary embodiments, FAB4.x series blends provide for increased electrophysiological response in electroantennogram (EAG) assays. EAG assays are known in the art (see e.g., Beck, J. J. et al (2009) *J. Agric Food Chem.* 2009; 57:3749-3753).

GAVA.x

In exemplary embodiments, blend formulations, referred to herein as the "GAVA.x series blends", comprise a mixture of four volatiles, hexanal (HXAL), octanal (OCAL), nonanal (NOAL), 3-octen-2-one (3O2O), in a relative ratio of 6:2:3:1. In some exemplary embodiments ratios of the four volatiles can vary. Indeed, in some exemplary embodiments the relative ratio of hexanal (HXAL), octanal (OCAL), nonanal (NOAL), 3-octen-2-one (3O2O) varies as [4.5-7.5]:[0.5-3.5]:[1.5-4.5]:1.

Thus in an exemplary embodiment, GAVA.1 blend comprises hexanal (HXAL), octanal (OCAL), nonanal (NOAL), 3-octen-2-one (3O2O), in a relative ratio of 15:4:6:2 (see Table 2, below). In another exemplary embodiment, GAVA.7 blend comprises hexanal (HXAL), octanal (OCAL), nonanal (NOAL), 3-octen-2-one (3O2O), in a relative ratio of 14:4:8:3.

In some exemplary embodiments, GAVA.x series volatile blends are used to attract navel orangeworm moths. In other exemplary embodiments, GAVA.x series blends are used to induce ovipositional disruption in female navel orangeworm moths. In still other exemplary embodiments, GAVA.x series blends provide for increased electrophysiological response in electroantennogram assays.

Not all of the formulations listed in Table 2 are GAVA.x series blends as disclosed herein above. GAVA.6 while not conforming to the formulation disclosed herein above is none-the-less effective for attracting and inducing ovipositional disruption in NOW. Furthermore, GAVA.6 provides for increased electrophysiological response in electroantennogram assays.

TABLE 2

Formulations and ratios for the GAVA.x series.

| VOC | CODE | GAVA.1 | GAVA.2 | GAVA.3 | GAVA.4 | GAVA.5 |
|---|---|---|---|---|---|---|
| 1 Hexanal | HXAL | 15 | 8 | 10 | | |
| 2 Heptanal | HPAL | | | | | |
| 3 Octanal | OCAL | 4 | 2 | 7 | | |
| 4 Nonanal | NOAL | 6 | 3 | 4 | | |

TABLE 2-continued

Formulations and ratios for the GAVA.x series.

| | VOC | | | | | |
|---|---|---|---|---|---|---|
| 5 | Decanal | DCAL | | | | |
| 6 | 3-Octen-2-One | 3O2O | 2 | 1 | | |
| 7 | 1-Octen-3-ol | OCOL | | | | |
| 8 | Ethyl hexanoate | ETHX | | | | 28 | 6 |
| 9 | Ethyl octanoate | ETOC | | | | 26 | 4 |
| 10 | 2-Heptanone | 2HPT | 1 | 0 | 5 | |
| 11 | Ethyl butyrolactone | ETBL | | | 4 | 1 |
| 12 | 2-Pentyl furan | 2PTF | 2 | 1 | 6 | 2 |
| 13 | 2-Butyl furan | 2BUF | | | 9 | 1 |
| 14 | Limonene (D) | LIMO | | | | 11 | 2 |
| 15 | Acetic acid | ACOH | | | | 3 |
| 16 | Hexanoic acid | HXOH | | | | 42 |

| | VOC | GAVA.6 | GAVA.7 | GAVA.8 | GAVA.9 | GAVA.10 | GAVA.11 |
|---|---|---|---|---|---|---|---|
| 1 | Hexanal | | 14 | 12 | | | |
| 2 | Heptanal | | 1 | 1 | | | |
| 3 | Octanal | | 4 | 8 | 2 | 1 | 1 |
| 4 | Nonanal | 1 | 8 | 8 | 12 | 7 | 7 |
| 5 | Decanal | | 3 | 3 | 1 | 1 | 1 |
| 6 | 3-Octen-2-One | 1 | 3 | 6 | 15 | 17 | 32 |
| 7 | 1-Octen-3-ol | 1 | | | | | |
| 8 | Ethyl hexanoate | | | | | | |
| 9 | Ethyl octanoate | 1 | | | | | |
| 10 | 2-Heptanone | | | | | | |
| 11 | Ethyl butyrolactone | | | | | | |
| 12 | 2-Pentyl furan | | | | | | |
| 13 | 2-Butyl furan | | | | | | |
| 14 | Limonene (D) | | | | | | |
| 15 | Acetic acid | | | | | | |
| 16 | Hexanoic acid | | | | | | |

BLND.x

Blend formulations of the BLND.x series comprise five volatiles hexanal(HXAL):octanal(OCAL):nonanal (NOAL): acetophenone (ACEP):phenol(PHOL) in ratios as disclosed herein.

In one exemplary embodiment, the blend of volatile organic compounds is effective for ovipositional disruption in the female navel orangeworm moth. The blend comprises hexanal:octanal:nonanal:acetophenone:phenol a relative ratio of 1:1:2:2:1.

In another exemplary embodiment the blend of volatile organic compounds effective for ovipositional disruption in the female navel orangeworm moth comprises hexanal:octanal:nonanal:acetophenone:phenol in mixed in a relative ratio of 1:1:2:4:1.

In another exemplary embodiment the blend of volatile organic compounds effective for ovipositional disruption in the female navel orangeworm moth comprises hexanal:octanal:nonanal:acetophenone:phenol in mixed in a relative ratio of 1:1:3:6:1

In some exemplary embodiments, increasing the relative proportion of acetophenone (ACEP) increases the effectiveness of the volatile blend.

In some exemplary embodiments, BLND.x series volatile blends are used to attract navel orangeworm moths. In other exemplary embodiments, BLND.x series blends are used to induce ovipositional disruption in female navel orangeworm moths. In still other exemplary embodiments, BLND.x series blends provide for increased electrophysiological response in electroantennogram assays.

III. Navel Orangeworm Traps

Insect traps suitable for trapping NOW either for monitoring or control are well known in the art (see e.g., U.S. Pat. No. 8,028,467; U.S. Pat. No. 7,856,753; U.S. Pat. No. 7,655,253, etc).

In one embodiment the invention is an apparatus that causes mating disruption among insect pests that includes a movable housing or device that can be strategically placed within an area needing treatment. The apparatus includes a source of at least one volatile organic blend as disclosed herein contained within the housing and a dispenser that is adapted to initiate the controlled release of the composition over an area of treatment in response to one or more control signals. The apparatus may be, unpowered, self-powered by batteries or may have some other external power source such as solar power.

In some exemplary embodiments, the volatile blend or blends is/are microencapsulated, by methods known in the art (see e.g., Bakan, J. A. *Microencapsulation Using Coacervation/Phase Separation Techniques*. In Controlled Release Technology: Methods, Theory, and Application; Kydonieus, A. F., Ed.; CRC Press: Boca Raton, Fla., 1980; pp 83-105; and Herbig, S. M, et al. (1987) Am. Chem. Soc. Div. Polym. Chem. Prepr. 1987, 28, 92-9, each of which are incorporated herein by reference). However, any suitable method known in the art for dispersal/dispensation of volatile blends disclosed herein for luring and/or trapping may be used.

IV. Methods for Attracting Navel Orangeworm

Insect traps are typically used to monitor or directly reduce insect populations. Traps may reduce insect populations directly or may reduce future populations by negatively affecting the reproductive capacity of a present generation of insects e.g., through the use of egg traps and/or ovipositional disruption. Thus, one embodiment, the volatile organic blends disclosed herein, are used to attract and trap NOW. However, in other exemplary embodiments, the volatile blends disclosed herein are used in combination with other NOW attractants known in the art e.g., in combination with almond meal, to attract navel orangeworm moth. In other exemplary embodiments, egg traps are baited with volatile blends disclosed herein to effect ovipositional disruption.

In an exemplary embodiment, effective attractant ability is indicated when a NOW trap baited with a volatile blend as disclosed herein captures more NOW than an unbaited trap. Similarly, in other exemplary embodiments, effective ability to induce ovipositional disruption is indicated when a NOW egg trap baited with a volatile blend as disclosed herein captures more NOW eggs than an unbaited trap.

The following examples are offered to illustrate, but not to limit the invention.

EXAMPLES

Example 1

The following example illustrates formulation of a synthetic blend of volatile organic compounds suitable for inter alia ovipositional disruption of the female navel orangeworm.

Methods and Materials for Example 1

Orchard.

The collection site in the southern Central Valley was located near Lost Hills, Calif. (Kern County) on the property of Paramount Farming Company. The plot, ca. 160 acres, contained the almond varieties Nonpareil, Carmel, and Monterey, *Prunus dulcis* (P. Mill) D.A. Webb, in a 2:1:1 ratio, and was contiguous to ca. 881 acres of Butte and Padre (1:1) varieties to the East. The collection boxes (duplicated per run) were placed in the tree rows of Nonpareil, and spaced ca. 85 m apart from each other in north/south line.

Volatile Collections.

Volatiles were absorbed onto Tenax® via use of a large-scale volatile collection system (see Appendices and Supplementary Material for color pictures) comprised of the following: glass cartridges containing Tenax® (10 g) fastened inside of a closed cylinder with a port for vacuum attachment and a screened port open to ambient orchard air; the cartridge was attached via Teflon® 0.64 cm tubing to a high-volume (4-5.5 l/min), 12 VDC, eccentric diaphragm pump (Schwarzer Precision, Germany) powered by an AGM-92AH battery (West Marine, Richmond, Calif.) and an 18 VDC, 1.8 Amp solar panel (PowerUp, Baltimore, Md.). The vacuum pump, electronic controller, and pump switch were contained within a 30.5×30.5×10 cm sealed box with a screened exit for pump air exhaust. The solar panel was secured to a telescoping aluminium pole and raised above the tree canopy. The cylinder, box, and pole were all secured to an 8.6×8.6×244 cm wooden post dug 60 cm into the ground and within the tree line to avoid interference with orchard heavy equipment. Degree days were based on almonds and a biofix date of Jan. 1, 2009 for NOW at the corresponding collection location (UC IPM, 2010).

Volatile Analyses.

Upon completion of VOC collection, the Tenax® cartridges were sealed and transported to the laboratory for VOC desorption and analyses following published protocols (Beck et al., 2008). A typical VOC analysis included: desorption with diethyl ether, concentration of extracted volatile solution to ca. 1 ml via warm water bath and Vigreux condenser, and transfer of desorbed volatiles onto a J&W Scientific (Folsom, Calif.) DB-Wax column (60 m×0.32 mm i.d.×0.25 µm), and a J&W Scientific DB-1 column (60 m×0.32 mm i.d.×0.25 µm) installed on one of two HP-6890 gas chromatographs (GC) coupled to HP-5973 mass selective detectors (MS, Palo Alto, Calif.). Desorbed volatiles were analyzed with the following methods. For DB-Wax: injector temp, 200° C.; split mode; inlet temp, 200° C.; constant flow, 3.0 ml/min; oven settings, initial temp, 40° C.; hold time, 0.0 min; ramp one, 4° C./min; final temp, 200° C.; hold time, 15 min. For DB-1: injector temp, 200° C.; split mode; inlet temp, 200° C.; constant flow, 2.0 ml/min; oven settings, initial temp, 40° C.; hold time, 0.0 min; ramp one, 4° C./min; final temp, 250° C.; hold time, 5 min. MSD parameters: source temp, 230° C.; MS source temp 150° C.; EI mode, 70 eV; solvent delay, 6 min; scan group 1, 40-400 amu; scan group 2 at 20 min, 40-450 amu. NIST, Wiley, and internally generated databases were used for fragmentation pattern identification. The retention indices (RIs) were calculated using a homologous series of n-alkanes on the DB-Wax and DB-1 columns. Volatile identifications were verified by injection of authentic samples and comparison to retention times of an internally-generated list of volatiles on identical columns. Each experiment was duplicated in field and injected onto separate columns for RI comparison purposes.

Data from GC-MS analyses were transferred to Microsoft Excel® for comparison of retention times and compound identification for same-column analysis. Calculated RIs were used to assist in compound identification and to perform comparison of DB-1 to DB-Wax column results. Inclusion of a VOC into Table 3 was based upon presence in both GC analyses. VOCs were quantified via the following: concentrated samples were adjusted to 2.0 ml with diethyl ether and an aliquot of 250 µl of the VOC sample was combined with 250 µl of an internal standard solution (3 µg/ml cyclodecanone in ether); samples were analyzed via GC-MS with injections of 1.0 µl at a 1:1 split. Standard calibration curves were obtained using four concentrations over the range of 0.15 to 30.0 µg/ml and the results averaged (linear regression analysis, $R^2=1$).

Test Insects.

Navel orangeworm moths, *Amyelois transitella* (Walker) (Lepidoptera: Pyralidae) used for bioassays were from a laboratory-reared colony established in 2009 from larvae and adults emerging from field-infested walnuts of various varieties collected at the USDA-ARS National Clonal Germplasm Repository, Wolfskill Expermental Station in Winters, Calif. Both larvae and eggs, laid from emergent mating pairs, were placed in 1 gal glass jars and reared until adult emergence on an established red-flake wheat bran-based diet (USDA-ARS, SJVASC, Parlier, Calif.) (Tebbets et al., 1978). The rearing room was maintained at 28-30° C., 60-70% RH, and a 16:8 L:D cycle. Upon emergence adults were transferred for mating to 1 gal glass jars with wire-screen lids, paper towels, and a cotton-plugged vial of 4% honey water. For EAG analysis moths were sexed and females or males were placed individually in clear plastic 30 ml portion-cups with lids. For flight tunnel studies, after 2-6 days of mating opportunity, groups of 20 mated females were released into the downwind chamber of the flight tunnel for each test, along with 20 mature males for certain tests.

Electroantennogram Bioassays.

The EAG experiments were performed by similar protocols described previously (Beck et al., 2009, supra). The antennae of sexed NOW were excised, positioned on a fork electrode using electrode gel, and connected to an IDAC-4 acquisition controller and electrophysiological amplifier using PC-based software (Syntech, Kirchzarten, Germany). The antennae were humidified with a stream of purified air bubbled through distilled water at a flow rate of 200 ml/min. The individual compounds for EAG analysis (50 µg; 10 µl of a 5 µg/µl solution in pentane) were loaded onto oven-dried 0.64 cm assay discs, allowed to air-dry for five min, inserted into 14.6 cm Pasteur pipets and the ends temporarily capped with parafilm. Blend V consisted of the volatiles hexanal, octanal, nonanal, acetophenone, and phenol in a 1:1:2:2:1 equimolar concentration (total 50 μg; 10 μl of a 5 μg/μl solution in pentane). For almond meal analyses, 3.1 mg was placed in a Pasteur pipet containing very lightly packed glass wool. Negative control (NegCtrl) discs were prepared using a similar method, but with 10 μl of pentane prior to solvent evaporation. Positive control (PosCtrl) discs were prepared using the major sex pheromone component (Z,Z)-11,13-hexadecadienal (50 μg, Suterra LLC, Bend, Oreg.). The pipets loaded with the individual compounds were attached via tubing to a stimulus controller unit (Syntech). The antennae were exposed to each compound by a two-second puff of air and the resulting response recorded. The antennal stimulation was duplicated for each VOC with a one minute delay between puffs. Each antennal pair were exposed to five to seven duplicated puffs after 10 min from the first excision performed and in the order PosCtrl, compound A, compound B, NegCtrl, compound C, compound D, and PosCtrl. Each run lasted no longer than 30 min from excision to completion of run on the antennal pair. The orders of test compounds were randomized for each set of antennae. Female and male NOW antennal responses (μV) to the individual VOCs were normalized using the equation EAG raw response—NegCtrl. The values shown in Table 3 are the normalized values of the 1$^{st}$ puff replicated responses (N values provided in each Table). EAG experiments for the total collected ambient volatiles consisted of the concentrated volatiles in diethyl ether (80 μg) on oven-dried 0.64 cm assay discs and diethyl ether as the NegCtrl discs.

Flight Tunnel Bioassay.

The flight tunnel experiments were performed in a rectangular (237×88×87 cm) tunnel constructed from tempered glass with air inlet and exit galvanized sheet-metal enclosures. Inlet airflow was generated by a variable-speed box fan set at medium speed (ca. 45 cm/sec), with airflow filtered through an activated charcoal-coated, fiberglass filter (Airguard Industries, Inc., Louisville, Ky.) then through a series of horizontally stacked plastic drinking straws to generate a laminar, yet slightly turbulent airflow. The effluent air from the tunnel was swept into two fume hoods located at the exit of the downwind enclosure. Flight tunnel dual-choice bioassays were performed using two sticky traps suspended at the ends of a rotating arm (80 cm brass tubing) powered by an AC motor (Herbach & Rademan Co., Moorestown, N.J.) at 0.25 rpm. The rotating arm was attached within the tunnel 68 cm above the floor and 40 cm from the upwind end. Traps were triangular prism shaped "delta traps" (9.5 cm/side×11.5 cm long) of black textured plastic sheeting from thick folder cover sheets and sticky glue-coated (The Tanglefoot Co., Grand Rapids, Mich.) liners cut from identical plastic sheeting. Blend V (5 mg, 5 mg/100 μl solution in pentane) and controls for bioassays were impregnated into gray plastic septa placed on the sticky insert, with new septa for each experiment, excluding fresh almond meal (63 mg) (Liberty Vegetable Oil Co., Santa Fe, Calif.) which was transferred to a scintillation vial cap and placed upon the sticky insert.

At the end of a 16 h light phase the 20 mated female moths were released from a shelf placed 70 cm above the tunnel floor and ca. 260 cm from the rotating arm, at the downwind enclosure-chamber. Once the moths were released the room lights were dimmed to darkness over a 45 min period. The flight tunnel room was maintained at 24-26° C., 60-70% RH. A sole light source 7.5 W, 80 VDC, 2 lux, red light bulb was used for observations during bioassays. Each replicate was performed for the entire scotophase, the traps removed, and captured moths were counted, sexed, and females checked for mating status by dissection of bursa copulatrix and presence of spermatophore(s). Eggs deposited on both the inside ceiling and outer surfaces of the traps were counted at the conclusion of each experiment. The numbers of moths captured and eggs laid were arc-sine transformed (if necessary) for normalization and then analyzed by one-way ANOVA, with significant treatment pairs being analyzed by the paired t-test (SigmaStat, 2009).

Results for Example 1

A total of 25 volatiles were collected in minor to major amounts, separated via GC-MS, and identified (Table 3). The volatiles hexanal, octanal, nonanal, benzaldehyde, acetophenone, ethyl benzoate, methyl salicylate, and phenol were consistent throughout the times collected during the season and in relatively high orchard volatile densities (>20 ng/m$^3$). A number of volatiles were either transient and/or at a very low relative concentration within the ambient orchard environment.

TABLE 3

Ambient almond orchard volatiles from Kern County, California collected during the 2009 growing season.

| | | DB-Wax$^a$ | | | Ambient Almond | | | |
|---|---|---|---|---|---|---|---|---|
| | | | RI | | Volatile Amounts (ng/m$^3$)$^b$ | | | |
| # | Compound ID | RT | calc'd | Lit | Collection 1 | Collection 2 | Collection 3 | Collection 4 |
| 1 | hexanal | 6.48 | 1077 | 1077 | 26.8 | 49.3 | 31.1 | 23.3 |
| 2 | undecane | 6.76 | 1088 | 1100 | 0.0 | 0.0 | 0.0 | 7.0 |
| 3 | curnene | 8.77 | 1167 | 1168 | 3.0 | 5.3 | 0.0 | 3.5 |
| 4 | heptanal | 9.11 | 1180 | 1180 | 12.2 | 13.1 | 11.4 | 13.1 |
| 5 | limonene | 9.48 | 1194 | 1195 | 3.7 | 0.6 | 0.0 | 0.0 |
| 6 | p-cymene | 11.59 | 1266 | 1264 | 1.8 | 4.8 | 4.5 | 6.9 |
| 7 | octanal | 12.17 | 1285 | 1284 | 78.1 | 108.2 | 49.6 | 50.1 |
| 8 | nonanal | 15.42 | 1390 | 1389 | 237.4 | 338.4 | 161.2 | 169.4 |
| 9 | acetic acid | 17.29 | 1451 | 1447 | 11.1 | 3.9 | 13.9 | 11.2 |
| 10 | dacanal | 18.65 | 1495 | 1495 | 3.8 | 0.0 | 18.1 | 21.7 |
| 11 | benzaldehyde | 19.20 | 1515 | 1516 | 306.8 | 165.3 | 306.6 | 1971.5 |
| 12 | benzonamite | 21.63 | 1595 | 1597 | 3.9 | 1.7 | 3.5 | 10.0 |
| 13 | γ-pentalactone | 21.78 | 1601 | 1600 | 3.4 | 8.1 | 10.8 | 6.2 |
| 14 | methyl benzoate | 22.19 | 1615 | 1616 | 7.7 | 9.3 | 14.8 | 7.0 |
| 15 | sabina ketone$^c$ | 22.51 | 1626 | n/a | 12.6 | 0.0 | 5.3 | 3.2 |
| 16 | phenylacetaldehyde | 22.70 | 1633 | 1636 | 11.9 | 10.4 | 19.0 | 25.9 |

TABLE 3-continued

Ambient almond orchard volatiles from Kern County, California collected during the 2009 growing season.

| | | DB-Wax[a] | | Ambient Almond | | | |
|---|---|---|---|---|---|---|---|
| | | | RI | Volatile Amounts (ng/m$^3$)[b] | | | |
| # | Compound ID | RT | calc'd | Lit | Collection 1 | Collection 2 | Collection 3 | Collection 4 |
| 17 | acetophenone | 22.98 | 1642 | 1645 | 151.5 | 224.8 | 263.8 | 355.4 |
| 16 | ethyl benzoate | 23.51 | 1661 | 1661 | 51.9 | 59.7 | 23.3 | 31.8 |
| 19 | salicylaldehyde | 23.72 | 1668 | 1673 | 5.4 | 7.2 | 5.3 | 9.8 |
| 20 | γ-hexalacetone | 24.39 | 1691 | 1699 | 4.3 | 9.6 | 13.9 | 13.5 |
| 21 | naphthalene | 25.44 | 1730 | 1734 | 0.0 | 0.0 | 1.4 | 3.0 |
| 22 | methyl salicylate | 26.46 | 1767 | 1771 | 122.7 | 191.7 | 76.7 | 77.5 |
| 23 | γ-methylnaphthaiene | 28.42 | 1841 | 1848 | 0.0 | 11.8 | 14.8 | 0.0 |
| 24 | phenol | 32.48 | 2002 | 200 | 74.7 | 53.7 | 74.4 | 87.7 |
| 26 | p-anisaldehyde | 32.84 | 2017 | 2024 | 3.5 | 0.0 | 0.0 | 11.3 |
| | Degree Days | | | | 482-537 | 1536-1732 | 1752-1930 | 2592-2317 |
| | Collection Dates | | | | Apr. 23- | Jun. 30- | Jul. 7- | Aug. 11- |
| | (days) | | | | May 5 (12) | Jul. 7 (7) | Jul. 15 (8) | Aug. 21 (10) |

[a]RI calculated relative to n-alkanes on DB-Wax and compared to literature and internally generated data base values.
[b]Ambient volatile density calculated using total amount each volatile per volume of air collected (total number of minutes × flow rate for each unity).
[c]Tentative assignment; compound not available for authentication or EAG analysis.

All volatiles, excluding ones not readily available, in Table 3 underwent an initial EAG screening for both male and female NOW (N=2) to screen for biological activity. Volatile components demonstrating a moderate female EAG response and constant presence throughout the volatile collection period provided a foundation for initial blend formulations and subsequent in vitro bioassay analysis. The fifth blend formulation, Blend V with the ratio of 1:1:2:2:1 hexanal:octanal:nonanal:acetophenone:phenol, was taken forward for rigorous EAG bioassay and flight tunnel studies.

EAG studies comparing Blend V, almond meal, and a combination of the two showed an electrophysiological preference for Blend V versus almond meal. When Blend V was added to almond there was no significant change in EAG response relative to Blend V. The EAG antennal recordings of female NOW to the ambient almond orchard volatile bouquet (N=2) indicated relatively strong electrophysiological response to the semiochemical medium.

The no-choice flight tunnel studies of male and female NOW responses to Blend V and almond meal provided no statistically significant differences in the number of female NOW captured on the sticky traps (Table 4), and only slightly better male captures for almond meal, albeit very small numbers. However, for both dual-choice and no-choice studies female NOW exhibited ovipositional preference for the Blend V formulation over the current field female monitoring standard, almond meal (Table 4).

TABLE 4

NOW moths caught and eggs deposited overnight flight tunnel studies. Each experiement consisted of the release of 20 mated moths, male and female, each 2-6 days old.

| | Treatment Pairs[a] | | | | | | |
|---|---|---|---|---|---|---|---|
| | Experiment #1 | | Experiment #2 | | Experiment #3 | | |
| | Almond meal | Control | Blend V | Control | Almond meal | Blend V | Statistics |
| Males Captured N = 6 | 1.5 ± 0.8 | 0.2 ± 0.2 | 0.1 ± 0.1 | 0.3 ± 0.3 | n/a | n/a | $F_{3,25} = 2.6$ P = 0.07 |
| Females Captured N = 9 | 3.3 ± 1.4* | 0.8 ± 0.5* | 5.0 ± 0.6*** | 0.9 ± 0.3*** | 6.1 ± 0.5 | 5.9 ± 0.4 | $F_{5,63} = 17.3$ P < 0.001 |
| Eggs Deposited N = 20 | 30.5 ± 10.1** | 12.8 ± 6.4** | 52.9 ± 7.1*** | 1.2 ± 0.9*** | 51.5 ± 6.4*** | 74.5 ± 8.2*** | $F_{4,63} = 14.6$ P < 0.001 |

[a]Experimental conditions; 63 mg almond meal, gray septa impregnated with 100 μl of pentane and allowed to evaprate tor control, or gray septa impregnated with 5 mg Blend V in 100 μl of pentane. which was allowed to evaporate prior to analysis. Mean values are paired. Treatments were significantly different by paired t-Tests: *P < 0.05; P < 0.03; *P < 0.001.
[b]Males not released The relative composition of the volatile bouquet is expressed in terms of 'orchard volatile density'. To determine density, a high-volume, high-efficiency eccentric diaphragm vacuum pump allowed for precise measurement of the flow rate, so that the total volume of air was known for each collection. Collected volatiles for a given volume were then desorbed, and quantified, via GC-MS, and the relative concentration of each volatile was calculated. This ability to determine volatile density facilitated the determination of accurate accurate ratios of semiochemicals (see e.g., Bruce et al., 2005; Pickett et al., 2007).

Of the 25 relevant volatiles collected from the almond orchards, eight were consistent throughout the collection periods, and in relatively high orchard densities. Benzaldehyde, a ubiquitous plant volatile commonly known as the primary component of bitter almond oil, was detected in the highest amount—165-1972 ng/m$^3$. Benzaldehyde, as well as all of the aldehydes, was detected as both the aldehyde and the corresponding acid. This is presumably due to air oxidation of the aldehydes while absorbed on the Tenax® medium. To verify this assumption, the aldehydes detected in this study were loaded onto a cartridge of Tenax® and placed in an oven at 38° C. with airflow of 4 l/min. The components were desorbed after 1 week and the corresponding acids were detected in varying amounts. Thus, the aldehyde amounts shown in Table 3 are understood to be a combination of both the aldehyde and acid form, and include the relative amounts for their detected associated acids. Despite its presence as the major volatile in all collections, both initial EAG studies and early blend formulations with benzaldehyde did not provide evidence for this component being necessary for electrophysiological stimulation to NOW.

The remaining consistent and major volatiles were acetophenone, ethyl benzoate, methyl salicylate, and phenol. Acetophenone, a ubiquitous volatile from several plant families (see e.g., El-Sayed, 2007), showed a progressive increase in ambient volatile presence over the growing season. In addition to its relatively high orchard density, acetophenone elicited a high EAG antennal response from female NOW of 397 µV, normalized, and for this reason was included in the blend formulation. Ethyl benzoate is a ubiquitous volatile emitted from numerous plants (El-Sayed, 2007), including almonds (Beck et al., 2008). A surprising addition to the blend formulation was phenol, for which this is the first report for its detection from almonds. Though the female NOW antennal EAG response to phenol was relatively moderate (78 µV, normalized) its inclusion into Blend V was made once it was noted phenol raised the female antennal response to the blend.

The change in emission patterns over the course of volatile collections suggests a dynamic versus static volatile medium encountered by insects throughout the growing season. An example of this dynamic emission was the change relative orchard volatile density of acetophenone, which showed an increase in emission over time, and nonanal which initially increased, but then dropped off toward the end of the collection times.

The behavioral response of male and female NOW toward Blend V were determined via flight tunnel studies. The moths' response to Blend V was evaluated against the current benchmark for female NOW monitoring in the field, almond meal. The EAG antennal response toward Blend V versus almond meal indicated electrophysiological preference toward Blend V; 487 µV normalized EAG response to Blend V compared to 100 µV normalized EAG response for almond meal. The combination of Blend V with almond meal did not provide any significant differences by EAG analysis. Furthermore, comparison of these two blends via flight tunnel corroborated the EAG results. The results provided in Table 4 show the female's in vitro preference for Blend V.

Experiment #1 evaluated the attractive capability of almond meal toward male and female NOW, using a blank as a control. In terms of capture, there was no significant differentiation between male and female NOW attracted to almond meal, though there was some increase in ovipositional activity for almond meal relative to the control trap. A 63 mg portion of almond meal was found to attract NOW moths and stimulate oviposition, while not overwhelming the flight tunnel volume or the dual-choice bioassays.

The second flight tunnel experiment evaluated the performance of Blend V relative to a blank control. Blend V did not appreciably attract more females when compared to the number of females from Experiment #1; however, there was a noticeable increase in the number of eggs deposited on the egg traps. Males did not show any interest in Blend V as an attractant in Experiment #2. The final flight tunnel experiment provided a dual-choice opportunity for the female NOW. Males were not evaluated in Experiment #3 per the results of the first two flight tunnel experiments. There was no difference in the ability of Blend V to attract females relative to almond meal; however, there was a distinct preference for ovipositional behavior toward Blend V.

Finally, an EAG experiment was performed on the collected bouquet of volatiles. The EAG response of female NOW toward the total composition of volatiles encountered by NOW moths for collections made in early May (Collection 1) and early July (Collection 2) showed relatively high antennal responses to the two bouquets.

Example 2

The following Example illustrates preparation of an exemplary FAB4.x series blend (FAB4.33) and an exemplary GAVA.x series blend and the use of these blends for trapping and effectively controlling female NOW.

An exemplary FAB4.x series blend, FAB4.33, was prepared in EtOAc as follows: 907 µL of 1-octen-3-ol (5.91 mmol, MW=128.2 g/mol, density 0.834 g/mL), 284 µL of ethyl benzoate (1.98 mmol, MW=150.2 g/mol, density 1.045 g/mL), 256 µL of methyl salicylate (1.98 mmol, MW=152.2 g/mol, density 1.174 g/mL), and 163 µL of ethyl palmitate (0.49 mmol, MW=284.5 g/mol, density 0.857 g/mL) were diluted in ethyl acetate to a total volume of 7.5 mL to provide a relative molar ratio of 12:4:4:1 of the active components in the solvent at a concentration of 200 mg/mL. Aliquots of 1 mL of this solution were then transferred to a plastic Nalgene container (8 mL, narrow-mouth bottle, Thermo Scientific) containing a plug of cotton (0.3 g, ca. 15×35×2 cm) and capped.

An exemplary GAVA.x series blend, GAVA.8, was prepared in EtOAc as follows: 490 µL of hexanal (4.08 mmol, MW=100.2 g/mol, density 0.834 g/mL), 47 µL of heptanal (0.34 mmol, MW=114.2 g/mol, density 0.817 g/mL), 430 µL of octanal (2.75 mmol, MW=128.2 g/mol, density 0.820 g/mL), and 473 µL of nonanal (2.75 mmol, MW=142.2 g/mol, density 0.827 g/mL), 192 µL of decanal (1.02 mmol, MW=156.3 g/mol, density 0.830 g/mL), 300 µL of 3-octen-2-one (2.04 mmol, MW=126.2 g/mol, density 0.857 g/mL) were diluted in ethyl acetate to a total volume of 7.5 mL to provide a relative molar ratio of 12:1:8:8:3:6 of the active components in the solvent at a concentration of 200 mg/mL.

For field trapping studies the caps of the Nalgene containers loaded with the lure formulations were exchanged for a cap with a ⅛" hole and suspended via wire on the inside of a delta trap and the trap placed in the canopies of trees of both almond and pistachio orchards. The traps are monitored weekly for the number of moths captured. At the end of the trapping study the moths are identified, sexed, and the female moths dissected to determine mating status. The lure formulations were replicated five per orchard (five in almonds, five in pistachios) and using almond meal as the positive control for female NOW capture.

NOW capture using the Nalgene container traps disclosed above loaded with different FAB4.x series blends and GAVA.x series blends are shown in Table 5 (below).

TABLE 5

Comparison of FAB4.x and GAVA.x formulations to the current standard for female NOW moth capture, almond meal.

| Blend | Male | Female | ALMm cf: | Kair/ALMm Ratio[a] |
|---|---|---|---|---|
| Pistachios | | | | |
| FAB4.25 EtOAc | 4 | 6 | 0 | 10.0 |
| FAB4.36 EtOAc | 2 | 4 | 0 | 10.0 |
| FAB4.33 EtOAc | 0 | 4 | 0 | 10.0 |
| GAVA.7 neat | 0 | 3 | 0 | 10.0 |
| GAVA.1 neat | 0 | 2 | 0 | 10.0 |
| FAB4.x components separate | 0 | 2 | 0 | 10.0 |
| GAVA.1 neat | 4 | 8 | 1 | 8.0 |
| GAVA.7 neat | 1 | 7 | 1 | 7.0 |
| GAVA.6 neat | 0 | 4 | 1 | 4.0 |
| FAB4.33 EtOAc | 0 | 3 | 1 | 3.0 |
| FAB4.33 EtOAc | 14 | 17 | 15 | 1.1 |
| FAB4.37 EtOAc | 3 | 2 | 2 | 1.0 |
| FAB4.33 EtOH | 11 | 11 | 15 | 0.7 |
| FAB4.33 EtOAc | 1 | 14 | 28 | 0.5 |
| GAVA.1 EtOAc | 0 | 6 | 14 | 0.4 |
| FAB4.33 neat | 3 | 3 | 7 | 0.4 |
| FAB4.32 EtOAc | 1 | 3 | 7 | 0.4 |
| FAB4.19 EtOAc | 7 | 6 | 15 | 0.4 |
| FAB4.19 EtOH | 3 | 5 | 15 | 0.3 |
| FAB4.32 EtOAc | 2 | 4 | 14 | 0.3 |
| FAB4.28 EtOAc | 0 | 4 | 14 | 0.3 |
| FAB4.31 EtOAc | 2 | 2 | 7 | 0.3 |
| FAB4.19 EtOAc | 2 | 5 | 28 | 0.2 |
| FAB4.26 EtOAc | 0 | 2 | 14 | 0.1 |
| FAB4.25 EtOAc | 1 | 2 | 14 | 0.1 |
| FAB4.33 EtOH | 2 | 2 | 28 | 0.1 |
| Almonds | | | | |
| FAB4.42 in EtOAc | 29 | 44 | 4 | 11.0 |
| GAVA.8 EtOAc | 0 | 4 | 1 | 4.0 |
| FAB4.42 in EtOH | 3 | 7 | 4 | 1.8 |
| FAB4.39 in EtOAc | 8 | 10 | 13 | 0.8 |
| FAB4.40 in EtOAc | 5 | 9 | 13 | 0.7 |
| FAB4.41 in EtOAc | 7 | 9 | 13 | 0.7 |
| FAB4.40 in EtOH | 7 | 5 | 13 | 0.4 |
| FAB4.41 in EtOH | 6 | 5 | 13 | 0.4 |

[a]Number of moths captured by the lures divided by the number of moths captured by the almond meal; values of bold 10 are divided by zero (infinity); ratios greater than 1 are more efficacious than the standard, almond meal.

In some exemplary embodiments, this same formulation is used but with ethanol (EtOH) as the solvent instead of EtOAc, or placed neat into the Nalgene container.

Another example of a possible trap set-up for a lure formulation was a similar ratio, but diluted in pentane (50 mg/mL), 0.200 mL transferred to a white rubber septum, and the pentane allowed to evaporate (1 min) at room temperature for a total loading of 5 mg per septum. For field trapping studies an individual septum were hung on the inside of a delta trap and placed in the field as previously described.

Example 3

The following Example illustrates preparation and testing of three blend formulations: Blend A, Blend B and Blend C. Efficacy of the Blends for attracting Navel Orangeworm were compared to almond meal in field trapping studies to determine their ability to attract adult navel orangeworm, *Amyelois transitella* Walker (Lepidoptera: Pyralidae). The five-component Blend A is comprised of five components: 1-octen-3-ol, ethyl benzoate, methyl salicylate, acetophenone, and racemic (E)-conophthorin; components common to all three blends. Blend C has six components comprising the five components of Blend A and additionally ethyl palmitate. Blend B comprises eight components comprising those of Blend A and further comprising 2-phenylethanol, humulene, and nonanal.

Materials and Methods for Example 3

Chemical Sources

Chemicals were purchased from commercial sources and used without further purification: 1-octen-3-ol (Bedoukian); methyl salicylate, 2-phenylethanol, humulene, and nonanal (SigmaAldrich); ethyl benzoate, acetophenone (Alfa Aesar); (+/−)-(E)-conophthorin (Contech); and ethyl palmitate (Eastman Chemical).

Blends

Blend A: 1-octen-3-ol:ethyl benzoate:methyl salicylate:acetophenone:conophthorin (12:4:4:1:1 ratio)—common components to all three blends; Blend B: further included 2-phenylethanol:nonanal:humulene (6:1:1:2:2:1:1:2 ratio); and Blend C: further included ethyl palmitate (12:4:4:1:2:1 ratio). Example of blend preparation (Blend A): Calculated for 2.5 g in 25 ml; 1-octen-3-ol (1.53 ml, 9.9 mmol); ethyl benzoate (0.48 ml, 3.3 mmol); methyl salicylate (0.43 ml, 3.3 mmol); acetophenone (0.10 ml, 0.8 mmol); and, conophthorin (0.13 ml, 0.8 mmol) were diluted in ethyl acetate (22.3 ml). Cotton plugs (ca. 350 mg) were inserted into 8 ml Nalgene bottles (VWR Scientific), 2 ml of blend (200 mg/2 ml) added, and bottles capped (Landolt and Alfaro 2001). In the field, caps were replaced with caps having a 1.5 mm hole.

Trials

A randomized complete block design with five replicates per treatment was configured in five almond orchards using orange plastic delta traps with glue liners (Suterra LLC). Traps with Nalgene bottles containing only cotton served as negative control, traps baited with almond meal (ca. 18.6 g) as a standard, and traps baited with three virgin females for male captures. Trap catches were collected after seven days, *A. transitella* adult moths were counted, and fresh blend bottles placed in the traps. Each moth capture experiment comprised two one-week trapping intervals: May interval, 5/13 to 5/27; June interval, 6/17 to 7/1; July interval 7/2 to 7/17; and, August, 8/5 to 8/19. Data from periods of no *A. transitella* pressure—blend and almond meal treatments having no captures and no or significantly low male capture in virgin female baited traps—were not included in the analysis. Trap data were analyzed with one-way ANOVA, and subsequent pairwise multiple comparisons with the Fisher LSD method.

Results for Example 3

Traps baited with almond meal captured three female and one male *A. transitella* over the test period and capture rates were not significantly different than blank traps, which caught one female (Table 6). For *A. transitella* captures of both males and females combined (*A. transitella* column, Table 6) blends significantly exceeding almond meal captures were: Blend A in all test intervals; Blend B in July only; and, Blend C in May, July, and August. For female moth captures (Female column) blends significantly exceeding almond meal captures were: Blend A in June; and, Blend C in July. For male moth captures (Male column) blends significantly exceeding almond meal captures were: Blend A and B in July; and, Blend C in August.

Average moth captures statistically exceeding almond meal over the pooled May through August intervals were (Overall blocks in Table 6): *A. transitella* captures, Blends/Lures A, B, and C; total female captures Blends/Lures A and C; and, total male captures Blends/Lures A, B, and C.

TABLE 6

Mean captures per trap per week of male and female *A. transitella* moths in traps baited with almond-based blends, Kern County, CA, 2011[a]

| Date | Date Range | Flight | Nτ | Treatment Lure A | Treatment Lure B | Treatment Lure C | Almond Meal | | |
|---|---|---|---|---|---|---|---|---|---|
| May | May 13-May 20 | 1 | 5 | 1.60 (±0.60) a | 0.60 (±0.40) a,b | 1.40 (±0.51) a,b | 0.20 (±0.20) b | F = 3.130 | df: 3.15; P = 0.047 |
| Jun. | Jun. 17-Jul. 1 | 2 | 7 | 1.14 (±0.26) a | 0.57 (±0.30) a,b | 0.29 (±0.29) b | 0.00 b | F = 4.000 | df: 3.24; P = 0.019 |
| Jul. | Jul. 2-Jul. 17 | 2 | 8 | 2.00 (±0.55) a | 2.33 (±0.31) a | 2.11 (±0.72) a | 0.22 (±0.22) b | F = 3.700 | df; 3.32; P = 0.005 |
| Aug. | tba | 3 | | | | | | | |
| Total | Jun. 13-Jul. 17 | | | 1.62 (+0.30) a | 1.33 (+0.44) a | 1.33 (+0.37) a | 0.14 (+0.30) b | F = 3.964 | df: 3.00; P = 0.011 |

[a]Capture values are given as means ± S.E. Data in rows followed by different sellers aree significantly different (P < 0.05), one way ANOVA followed by all pairweb multiple comparisons by Student Howman Koule method The June trapping interval demonstrated blend differential attraction with significantly greater numbers of female *A. transitella* captured with Blend A over that of Blend C (P=0.01). Numerically, all three Blends captured more males than females; however, statistically there was no significant difference with the lone exception of Blend C in the August testing interval (P<0.05).

Conclusion

Both male and female *A. transitella* attraction and capture activity were demonstrated by the almond volatile-based Blends A, B, and C in almond orchards with captures exceeding that of almond meal, the current standard bait for female monitoring. For combined male and female captures over the entire test period, all three blends demonstrated significantly higher captures rates than almond meal. For total female captures Blends A and C were nearly equal to each other and statistically exceeded almond meal. For total male captures all three blends statistically exceeded almond meal.

Blend A, the blend with the least number of components, consistently was effective at capturing adult *A. transitella*. This trend was also noted during unreported early-season trapping trials of formulations when Blend A captured 11.30 (±1.97) adults compared to almond meal 1.60 (±0.34).

All three Blends exhibited their highest captures in the July trapping interval during which the lowest number of male *A. transitella* were caught in the virgin-baited traps (17.8±6.5 per trap). One example of male/female preference was suggested with statistical difference in Blend C for the August trapping interval.

Subsequent blends were formulated with the intent of decreasing the number of requisite components. An exemplary active, blend started with the four components 1-octen-3-ol, ethyl benzoate, methyl salicylate, and ethyl palmitate. Another exemplary active blend is 1-octen-3-ol, ethyl benzoate, and methyl salicylate in a basic ratio of 3:1:1. In some exemplary embodiments ethyl acetate was used as a solvent to help stabilize the blend components.

Example 4

The following Example illustrates modifications to FAB4.x and GAVA.x series and their resultant field results:

FAB.x and GAVA.x blends were mixed with another component, conophthorin (CONO). CONO increased the efficacy of the blends in the FAB4 and GAVA series. This was somewhat unexpected as CONO alone is not attractive to NOW. Indeed, electroantennographic studies revealed that CONO was mildly active, albeit lower than the positive standard at that time. Subsequent field trapping screening studies of individual CONO between September 2 and Oct. 5, 2009 in both almond and pistachio orchards did not attract any NOW. Virgin female NOW-baited traps at the same time indicated pressures of NOW in the orchards.

Conophthorin (chemical name 7-methyl-1,6-dioxaspiro [4.5]decane, CONO) was reported by our group in the publication Beck et al., J Sci Food Agric 2008, 88, (8), 1363-1368. It was found that when mixed with the background volatiles of the FAB4.x and GAVA.x series efficacy of the lures improved.

CONO has been reported as a pheromone of bark beetles (J Chem Ecol 1995, 21, 143) and yellow jackets (Naturwissenschaften 1979, 66, 618). Some exemplary chemical structures and possible stereoisomers for CONO are shown below.

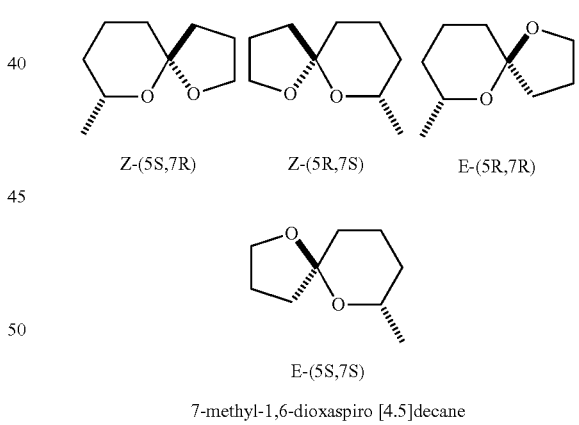

Z-(5S,7R)  Z-(5R,7S)  E-(5R,7R)

E-(5S,7S)

7-methyl-1,6-dioxaspiro [4.5]decane

In early trial studies (field trappings) preliminary blends were prepared with CONO in them and positive results in terms of the number of NOW moths captured (both female and male) were obtained using the preliminary blends. Data obtained using the preliminary blends were refined to formulate 5 blends (LURES A-F) for use in a year-long capture study.

The following blends were formulated and underwent an intensive year-long trapping study in almond and pistachio orchards (2011 season).

| Almonds | | OCOL | ETBN | MSAL | ETPM | ACEP | CONO | 2PEA | NOAL | HUMU |
|---|---|---|---|---|---|---|---|---|---|---|
| LURE A | FAB4.59 EtOAc | 12 | 4 | 4 | | 1 | 1 | | | |
| LURE B | FAB4.61 EtOAc | 6 | 1 | 1 | | 2 | 2 | 1 | 1 | 2 |
| LURE C | FAB4.62 EtOAc | 12 | 4 | 4 | 1 | 1 | 2 | | | |

| Pistachios | | HXAL | OCAL | NOAL | 3O2O | 2HPT | 2PTF | CONO |
|---|---|---|---|---|---|---|---|---|
| LURE D | GAVA.1 EtOAc | 15 | 4 | 6 | 2 | 1 | | 2 |
| LURE E | GAVA.18 EtOAc | 15 | 4 | 6 | 2 | | 2 | 2 |

| | | OCOL | ETBN | MSAL | ACEP | CONO |
|---|---|---|---|---|---|---|
| LURE F | FAB4.59 EtOAc | 12 | 4 | 4 | 1 | 1 |

Where OCOL is 1-octen-3-ol: ETBN is ethyl benzoate; MSAL is methyl salicylate, ACEP is acetophenone; CONO is conophthorin; 2PEA is 2-phenylethanol; NOAL is nonanal; HUMU is humulene; EtOAc is ethyl acetate; 2HPT is 2-heptanone; 2-PTF is 2-pentyl furan; 3O2O is 3-octen-2-one; ETPM is ethyl palmitate; HXAL is hexanal; OCOL is octanal.

EAG studies were be performed to determine the optimal amount of EtOAc (optimizing the ratios and amount of EtOAc). EtOAc is used as a solvent, albeit an active solvent. The current ratios were evaluated are on 4.59 and are as follows:

| | | OCOL | ETBN | MSAL | ACEP | CONO | EtOAc | |
|---|---|---|---|---|---|---|---|---|
| LURE F | FAB4.59 EtOAc | 12 | 4 | 4 | 1 | 1 | 275 | Current amount (10 mg components in 100 μL solution) |
| LURE F | FAB4.59 EtOAc | 12 | 4 | 4 | 1 | 1 | 198 | =10 mg components in 75 μL solution |
| LURE F | FAB4.59 EtOAc | 12 | 4 | 4 | 1 | 1 | 121 | =10 mg components in 50 μL solution |
| LURE F | FAB4.59 EtOAc | 12 | 4 | 4 | 1 | 1 | 244 | =10 mg components in 25 μL solution |
| LURE F | FAB4.59 EtOAc | 12 | 4 | 4 | 1 | 1 | 0 | neat |

TABLE 7

Total season-long (20 weeks from 5/20 to 10/14) captures in almond and pistachio orchards of male and female *A. transitella* moths in traps baited with host plant volatiles.

| | | Moths Captured | | |
|---|---|---|---|---|
| Orchard | Treatment | NOW Total | Female | Male |
| Almond | Blend A | 62 | 27 | 35 |
| | Blend B | 37 | 11 | 26 |
| | Blend C | 52 | 24 | 28 |
| | Meal | 8 | 7 | 1 |
| | Blank | 1 | 1 | 0 |
| Pistachio | Blend D | 3 | 3 | 0 |
| | Blend E | 2 | 2 | 0 |
| | Blend F | 32 | 20 | 12 |
| | Meal | 2 | 2 | 0 |
| | Blank | 0 | 0 | 0 |

Comparison of the week to week trials for Blend F showed no activity from May to early July, sporadic activity in July and August, and then some consistent activity in September. However, Blend F, when active, attracted female *A. transitella* when the almond meal did not. The positive results of Blend F provide evidence for kairomonal-based blend of components for attraction of *A. transitella* in pistachio orchards.

Example 5

The following Example illustrates testing of additional components for volatile blends for attraction and control of navel orangeworm (NOW).

The following components were identified by electroantennographic (EAG) studies. EAG experimentation, using the antennae of navel orangeworm male and female moths, provides an electrophysiological response to assist in screening large number of volatile components or blends of components for activity as an attractant.

Using the EAG responses of blends and components and corresponding field trapping results, correlations of other host plant volatile components have been drawn. The volatiles described below represent the components, in addition to the components listed in Blends A-C (see Example 3 above), that have been identified as effective by EAG analysis of volatiles from pistachio orchards and combined with various components from Blends A-C. Several blend formulations were tested (N=3-5) and the best responses are listed here.

For Male NOW EAG Responses:

Removal of MSAL and addition of limonene (LIMO) to Blend A to provide: OCOL:ETBN:MSAL:ACEP:CONO:LIMO (12:4:0:1:1:3; listed as PIST.8)

The male NOW EAG response to PIST.8 was 1,575 μV (cf: female response to Blend A=1,750 μV); PIST.8 (male response) and Blend A (female response) and are statistically equivalent. It is noted that more males overall were attracted to Blend A than females in field trapping studies.

Combination of a GAVA.x component, a FAB4.x component, and LIMO in a basic three component blend, LIMO:NOAL:CONO (3:2:1; listed as PIST.2) provided a male NOW EAG response of 1,690 µV.

The simple blend (PIST.2) with LIMO:CONO:NOAL in a 3:1:1 ratio keeps the 3:1 ratio of LIMO:CONO as above, with the addition of the GAVA.x component NOAL a stronger response from the male is elicited.

In general, an effective by EAG response is elicited in male NOW using a blend having a range for LIMO:CONO as a base to add onto between about 2:1 to 4:1. The NOAL is typically present in a range of between about 1 to 3.

A more complex blend that elicits strong responses to both male and female (PIST.8) the previously defined basic ranges for OCOL:ETBN of 3:1 and LIMO:CONO between about 2:1 to 4:1 as noted above. ACEP, when present is typically effective when present a relative molar ratio of between about 1 to 2. Thus, in an exemplary embodiment, an effective blend for attracting both male and female NOW comprises OCOL:ETBN:MSAL:ACEP:CONO:LIMO (12:4:0:1:1:3; listed as PIST.8)

Prophetic: combine PIST.8 and PIST.2 and/or components thereof with the major aldehydic component of the female sex pheromone, (Z,Z)-11,13-hexadecadinal (C16 A1d), to enhance the efficacy of C16A1d as a mating disruption ingredient.

For Female NOW EAG Responses:

The addition of the common pistachio-based volatiles LIMO, (Z)-ocimene (ZOCME), and α-pinene (APIN) (see e.g., Roitman et al. J Sci Food Agric 2011 91:934-942) to the current component CONO was successful in achieving female NOW EAG responses greater than male NOW EAG responses. Currently, the blend LIMO:CONO:APIN (3:1:1; listed as PIST.12) elicited a female NOW EAG response of 1,175 µV vs. a male NOW EAG response of 537 µV (statistically different by S.E.M.). The four component blend of LIMO:CONO:ZOCME:APIN (3:1:1:1; listed as PIST.11) elicited a female NOW EAG response of 1,195 µV vs. a male NOW EAG response of 620 µV (statistically different by S.E.M.). This greater response is of interest since other PIST.x blends (based on Blend A, but with addition of LIMO) showed the opposite with greater responses from male NOW antennae than female NOW antennae.

Thus, limonene (LIMO), (Z)-ocimene (ZOCME), and α-pinene (APIN) are added in exemplary embodiments to various blends to attract NOW. Typically the (−)-isomer of α-pinene is used. A racemic mixture can also be used. Additionally, EAG, or wind tunnel, or field studies will be performed on the (+)-isomer to determine the extent of response from NOW moths.

Thus in general following ratios are effective for attracting female NOW:

LIMO:CONO works well with a relative 3:1 as a base to add onto. A range of this basic requirement is in a range of between about 2:1 to 4:1. Effective ratios for ZOCME are between about 0.1 to 2 and effective ratios for APIN are between about of 0.1 to 3. Thus, in exemplary embodiments (which encompass the examples PIST.11 through PIST.17, all of which showed significant difference when compared to the corresponding male EAG responses) LIMO:CONO:ZOCME:APIN are present in a range of molar ratios of between about [2-4]:[1]:[0.1-2]:[0.1-3]. Thus, in an exemplary embodiment PIST.11 with LIMO:CONO:ZOCME:APIN in a 3:1:1:1 ratio is effective for attracting female NOW.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A blend of volatile organic compounds effective for attracting navel orangeworm moth, the blend comprising a mixture of 1-octen-3-ol (OCOL), ethyl benzoate (ETBN), methyl salicylate (MSAL), and ethyl palmitate (ETPM) wherein,
   the blend comprises a minimum relative molar ratio of 3:1 for OCOL:ETBN,
   the blend further comprising acetophenone (ACEP) and conophthorin (CONO) wherein the blend comprises ethyl benzoate (ETBN):methyl salicylate (MSAL):acetophenone (ACEP):conophthorin (CONO) in a 4:4:1:1 molar ratio.

2. The blend of volatile organic compounds of claim 1, wherein the formulation further comprises 7-methyl-1,6-dioxaspiro[4.5]decane (conophthorin, CONO).

3. The blend of volatile organic compounds of claim 1, further comprising: 2-phenylethanol, nonanal (NOAL) and humulene.

4. A trap for attracting male navel orangeworm, wherein the trap is baited with the blend of volatile organic compounds of claim 1.

* * * * *